United States Patent
Bulet et al.

(10) Patent No.: US 6,331,522 B1
(45) Date of Patent: Dec. 18, 2001

(54) ANTIBACTERIAL AND ANTIFUNGAL PEPTIDE

(75) Inventors: Philippe Bulet, Vendenheim; Charles Hetru, Illkirch Graffenstaden; Jules Hoffmann, Strasbourg; Laurence Sabatier, Molsheim, all of (FR)

(73) Assignee: Aventis CropScience SA, Lyons (FR)

( * ) Notice: Subject to any disclaimer, the term of this patent is extended or adjusted under 35 U.S.C. 154(b) by 0 days.

(21) Appl. No.: 09/524,675

(22) Filed: Mar. 13, 2000

Related U.S. Application Data

(63) Continuation of application No. 09/125,234, filed as application No. PCT/FR97/00295 on Feb. 17, 1997, now Pat. No. 6,127,336.

(30) Foreign Application Priority Data

Feb. 16, 1996 (FR) .................................................. 96 02168

(51) Int. Cl.[7] .......................... A61K 38/12; A61K 38/16; C07K 1/14; C07K 4/12; C07K 5/12
(52) U.S. Cl. ................................... 514/10; 514/3; 514/12; 530/317; 530/324
(58) Field of Search ................................... 514/10, 3, 12; 530/317, 324

(56) References Cited

PUBLICATIONS

Cociancich et al. (1993) *Biochemical and Biophysical Research Communications* 197:17.
Ehret–Sabatier et al. (1996) *Journal of Biological Chemistry* 271:29537.

*Primary Examiner*—Michael Borin
(74) *Attorney, Agent, or Firm*—Baker Botts L.L.P.

(57) ABSTRACT

The present invention provides a peptide with antibacterial and antifungal properties, and compositions containing the peptide. Methods of making and using the antibacterial and antifungal peptide are also provided.

2 Claims, No Drawings

ANTIBACTERIAL AND ANTIFUNGAL PEPTIDE

This is a continuation of application Ser. No. 09/125,234, now U.S. Pat. No. 6,127,336, filed Nov. 16, 1998 which is a 371 application of PCT/FR97/00295 filed Feb. 2, 1997.

The present invention relates to a novel protein-rich peptide with antibacterial and antifungal properties, and to compositions, which can be used in agriculture and in human or animal therapy, containing this peptide as active material. The invention also relates to processes for treating plants using these compositions, as well as to processes for preparing this peptide.

It has been known for a long time that insects have effective resistance to bacteria. This defence is largely based on the rapid synthesis of several families of peptides. This defence is due to is the rapid synthesis of several families of peptides with a broad spectrum of activity. This synthesis is induced by a septic wound or by the injection of a low dose of bacteria. Among the antibacterial peptides induced, those best characterized are the insect cecropines and defensines. Several other antibacterial peptides have been partially characterized.

Apart from the insect class, little is known about other arthropods. Scorpions have existed far longer than insects in terms of philogeny.

A peptide has now been isolated, from an induction in the scorpion *Androctonus australis*, this peptide showing remarkable characteristics as well as antibacterial and antifungal properties.

More particularly, a first aspect of the invention relates to the peptide of formula I: SEQ ID NO: 1

```
Arg Ser Val Cys Arg Gln Ile Lys Ile Cys Arg
                                          Arg
                                          Arg
Tyr Pro Arg Asn Thr Cys Lys Tyr Tyr Cys Gly Gly
```

Hereinbelow, the molecule of formula I will be referred to as androctonine. This relatively small molecule contains 4 cysteine residues engaged in two intramolecular bridges.

Another aspect of the invention relates to a first process for obtaining and isolating the above peptide, in which the following are successively carried out:

a) hemolymph is taken from the scorpion *Androctonus australis*;

b) extraction is carried out by placing the *Androctonus australis* hemolymph obtained above in contact with an acid medium, with stirring, followed by centrifugation;

c) the supernatant is fractionated with separation by washing of the hydrophilic molecules and elution of the hydrophobic molecules with appropriate components on a separating column;

d) the extracts are purified;

e) the peptide is characterized.

The hemolymph is taken by incision of the cuticle. It is collected in a tube containing a protease inhibitor. After centrifugation to remove the blood cells, the plasma is stored at −30° C.

In a preferred manner, in the second step (extraction), the *Androctonus australis* hemolymph is placed in contact with an acidic medium consisting of an acidic solution of an acid (of pH 2). The solution can be a solution of an inorganic or organic acid such as, for example, trifluoroacetic acid. The extract obtained is then centrifuged under cold conditions at a speed of 30,000×g at 4° C. for 25 min.

Preferably, in the third step (fractionation), the extract is placed on a reverse-phase cartridge in order to carry out a solid-phase extraction. The water-soluble molecules are washed out with a dilute acid solution and the hydrophobic molecules are eluted with an appropriate eluent. Good results are obtained with trifluoroacetic acid for the washing and an eluent containing increasing amounts of acetonitrile in dilute acid solution.

Preferably, the fourth step (purification) is carried out with a suitable eluent which can be identical to or different from the one in the preceding stage.

Preferably, in the final step (characterization), the nature of the peptide is analyzed by the method of sequencing by Edman degradation (Acta Chemica Scandinavia 10 (1956) pp. 761–768). According to this method, the following structures are obtained: SEQ ID NO: 2

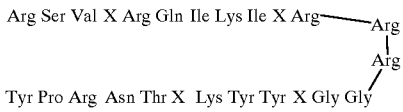

No signal was detectable in positions 4, 10, 16 and 20 (Edman degradation). The presence of cysteines in these positions was shown by mass spectrometry, the structure thus obtained being as follows: SEQ ID NO: 1

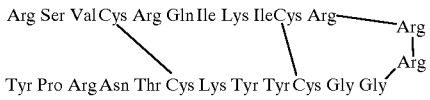

The measured masses for androctonine above are, respectively:

3076.65±0.24 Da

However, the masses calculated on the basis of sequencing data are, respectively:

3080.65±0.24 Da

The difference in mass corresponds to the formation of two intramolecular disulfide bridges.

In order to establish the connectivity of the disulfide bridges, the molecule was cleaved with an enzyme, Lys-C endoproteinase, which breaks the peptide chain after lysine. The peptides obtained were isolated and mass spectrometry showed that they were two peptides linked by a disulfide bridge. The sequences deduced were Arg Ser Val Cys Arg Gln Ile Lys plus Cys Thr Asn Arg Asn Pro Tyr and Ile Cys Arg Arg Arg Gly Gly Cys Tyr Tyr.

The connectivity of the disulfide bridges is thus established and cysteine 1 is linked to cysteine 4, cysteine 2 to cysteine 3. This result can be schematized thus: SEQ ID NO: 1

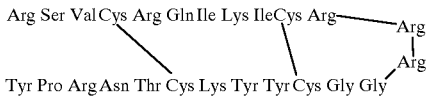

These good correlations confirm the proposed sequences.

The peptides according to the invention can also be obtained without difficulty according to a second process, by FMOC chemical synthesis (Atherton and Sheppard R. C. (1989), Solid Phase Peptide Synthesis (IRL, Oxford, UK)) followed by renaturing in 100 mM ammonium acetate solution at pH 8.5 for 24 hours with stirring at room temperature. The androctonine obtained has the same chromatographic properties as the native molecule and the connectivity of the disulfide bridges is identical to that of the natural molecule. The mass measured after renaturing (3076.61±0.67) is very similar to that of the native molecule. The synthetic molecule has the same antibacterial activity as the native molecule on the bacterium *Micrococcus liteus*.

All of the antibacterial and hemolytic tests are carried out with the synthetic molecule.

1. Androctonine has no lytic effect on porcine or bovine red blood cells.
2. These molecules have antibacterial properties on Gram-negative and Gram-negative bacteria (cf. Table 1), phytopathogenic bacteria and phytopathogenic fungi.

The examples which follow illustrate the production and the antibacterial properties of the peptides and the compositions according to the invention.

EXAMPLE 1

Isolation and Characterization of the Peptide

The process is performed according to the following steps:

extraction and purification:

The hemolymph (3.8 ml) is taken by incision of the cuticle. It is transferred into a tube, which is kept cold, in the presence of a protease inhibitor (aprotinine) and then centrifuged at 30,000×g for 25 minutes at 4° C. The supernatant thus obtained is immediately subjected to various purification steps.

Fractionation of the Extract on Sep-Pak C18 Cartridges

After depositing the extract on Sep-Pak C18 cartridges, the molecules of hydrophilic nature are removed by simple washing with 5 ml of water acidified with 0.05% trifluoroacetic acid (TFA).

The hydrophobic molecules are eluted with 10, 40 and 80% solutions of acetonitrile in acidified water (0.05% TFA, 5 ml per cartridge).

The fractions collected are named "10% elution", "40% elution" and "80% elution" and are concentrated under vacuum. The fractions are then reconstituted with HPLC-grade water before HPLC analysis.

HPLC Purification of the Molecules with Antibacterial Activity

First Step

The "40% elution" fraction is analyzed on an Aquapore OD 300 C18 reverse-phase column with a linear gradient of from 2 to 52% acetonitrile in acidified water (0.05% TFA) over 90 minutes (i.e. an increase of 0.44% acetonitrile per minute) at a flow rate of 1 ml/min.

The resulting active fractions are then purified on a "high pressure inert" (HPI) Delta Pak C18 column (150*3.9 mm).

The elution is carried out in a linear two-phase gradient of from 2 to 11% acetonitrile in acidified water (6 mM HCl) over 10 minutes and from 11 to 21% over 50 min at a flow rate of 1 ml/min. The purity of the active fraction is controlled by capillary electrophoresis before determination of the sequence by Edman degradation and analysis by mass spectrometry.

EXAMPLE 2

In vitro Test: Measurement of the Antibacterial Activity by Microspectrophotometry Pure each strain of bacteria used (*E. coli*; *M. luteus*), an isolated column is suspended in 10 ml of DIFCO PB medium (Poor Broth, Luria Bertani medium free of yeast extract) and incubated at 30° C. overnight with slow stirring.

The bacteria to be tested are brought to an is optical density at 600 nm of 0.001 in fresh culture medium. 10 µl of each fraction is deposited in microtitration plates in the presence of 100 µl of the bacterial suspension. After incubation for 24 hours at 25° C., the growth is evaluated by measuring the absorbance at 600 nm using a microtitration plate reader.

Under these conditions, a 50% inhibition is observed at the concentrations, expressed in µM, indicated in the following table:

TABLE 1

| Bacteria | Gram +/− | Androctonine MIC (µM) |
|---|---|---|
| Micrccoccus luteus | + | 0.6–1.5 |
| Aerococcus viridans | + | 0.3–0.6 |
| Bacillus subtilis | + | 1.5–3.0 |
| Staphylcccccus aureus | + | 15–30 |
| Clavibacter michi ganensis | + | 6–15 |
| Escherichia coli D22 | − | >30 |
| Escherichia coli D31 | − | 3–6 |
| Escherichia coli 1106 | − | 6–15 |
| Salmonella typhimurium | − | 3–6 |

Using the same protocol but with phytopathogenic bacteria, the following results are obtained:

TABLE 2

| Bacteria | Androctonine MIC (µM) |
|---|---|
| Clavibacter michiganensis | 6–15 |
| Pseudomonas syringae | 0.5–1 |
| Pseudomonas syringae pv syringae | 15–22 |
| Pseudomonas pisi | 6–15 |
| Pseudomonas maculicola | 3–6 |
| Pseudomonas valerianella | 15–22 |
| Pseudomonas syr phaseoli | 2–4 |
| Xanthomonas campestris pv campestris | 3–6 |
| Xanthomonas vesicatoria 687.3 | 1.5–3 |
| Xanthomonas vesicatoria B229RI | 1.5–3 |
| Xanthomonas phaseolica | 12 |

Using the same protocol but with phytopathogenic fungi, the following results are obtained:

TABLE 3

| | Androctonine MIC (µM) | |
|---|---|---|
| Fungi | without salts | with salts* |
| Alternaria dauci | 4.1–8.2 | 16–32 |
| Stemphyllium | 4–8 | 16–32 |
| Fusarium oxysporum L | 2–4 | >32 |
| Verticilium toreillis | 2–4 | >32 |
| Botrytis petuniae | 4–8 | >32 |
| Fusarium oxysporum meloni | 2–4 | — |

*medium supplemented with 1 mM $CaCl_2$ and 20 mM KCl

Among the crops which can undergo an antibacterial treatment using a compound according to the invention, mention may be made, for example, of rice, cereals, in particular wheat and barley, as well as arboricultural, fruit-yielding and legume-yielding plants.

Among the crops which can undergo an antifungal treatment using a compound according to the invention, mention may be made, for example, of Cucurbitaceae, floral cultures (petunia) and market garden crops (carrots, tomatoes, cabbages).

These results show the excellent antibacterial activity of the peptide according to the invention, which can be applied to the human, animal and plant fields.

The subject of the present invention is also compositions, which can be used as antibacterial agents, containing as active material(s) one (or more) compound(s) according to the invention as described above, mixed with solid or liquid agriculturally acceptable supports and surfactants that are also agriculturally acceptable. In particular, the common inert supports and the common surfactants can be used. These compositions cover not only compositions ready for application to the crop to be treated using a suitable device, such as a spraying device, but also concentrated commercial compositions which must be diluted before application to the crop.

These compositions can also contain other ingredients of any kind such as, for example, protective colloids, adhesives, thickeners, thixotropic agents, penetration agents, stabilizers, sequestering agents, etc. More generally, the compounds used in the invention can be combined with any solid or liquid. additive corresponding to the usual formulating techniques.

In general, the compositions according to the invention usually contain from 0.05 to 95% approximately (by weight) of a compound according to the invention (hereinafter referred to as active material), one or more solid or liquid supports and, optionally, one or more surfactants.

In the present specification, the term "support" denotes a natural or synthetic, organic or inorganic material with which the compound is combined in order to facilitate its application to the plant, to seeds or the soil. This support is thus generally inert and it should be agriculturally acceptable, in particular on the plant treated. The support can be solid (clays, natural or synthetic silicates, silica, resins, waxes, solid fertilizers, etc.) or liquid (water, alcohols, in particular butanol, etc.).

The surfactant can be an emulsifier, dispersant or wetting agent of ionic or nonionic type or a mixture of such surfactants. Mention may be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkyophenols or arylphenols), salts of sulfosuccinic acid esters, taurine derivatives (in particular alkyl taurates), polyoxyethylated phosphoric esters of alcohols or of phenols, fatty acid esters of polyols, derivatives containing sulfate, sulfonate and phosphate functions of the above compounds. The presence of at least one surfactant is generally essential when the compound and/or the inert support are not water-soluble and when the vector agent for the application is water.

Thus, the compositions for agricultural use according to the invention can contain the active materials according to the invention in a very wide range, of from 0.05% to 95% (by weight). Their surfactant content is advantageously between 5% and 40% by weight.

These compositions according to the invention are themselves in quite diverse solid or liquid forms.

As solid composition forms, mention may be made of powders for dusting (with a compound content which can be up to 100%) and granules, in particular those obtained by extrusion, compacting, impregnation of a granular support or by granulation of a powder (the compound content of these granules being between 0.5 and 80% for the latter cases), and effervescent tablets or lozenges.

The peptide according to the invention can also be used in the form of powders for dusting; a composition comprising 50 g of active material and 950 g of talc can also be used; a composition comprising 20 g of active material, 10 g of finely divided silica and 970 g of talc can also be used; these constituents are mixed together and ground and the mixture is applied by dusting.

As liquid composition forms or forms intended to constitute liquid compositions during application, mention may be made of solutions, in particular water-soluble concentrates, emulsifiable concentrates, emulsions, concentrated suspensions, aerosols, wettable powders (or powder for spraying), pastes and gels.

The emulsifiable or soluble concentrates usually comprise 10 to 80% active material, whereas the emulsions or solutions ready for application contain 0.001 to 20% active material.

In addition to the solvent, the emulsifiable concentrates can contain, when necessary, 2 to 20% of appropriate additives such as the stabilizers, surfactants, penetration agents, corrosion inhibitors, dyes or adhesives mentioned above.

Using these concentrates, emulsions of any desired concentration can be obtained by dilution with water, these emulsions being particularly suitable for application to crops.

The composition of a number of emulsifiable concentrates is given hereinbelow by way of example:

Example EC 1

| | |
|---|---|
| active material | 400 g/l |
| alkaline dodecylbenzene sulfonate | 24 g/l |
| nonylphenol oxyethylated with 10 molecules of ethylene oxide | 16 g/l |
| cyclohexanone | 200 g/l |
| aromatic solvent | qs 1 litre |

According to another emulsifiable concentrate formula, the following are used:

Example EC 2

| | |
|---|---|
| active material | 250 g |
| epoxidized plant oil | 25 g |
| mixture of alkyl aryl sulfonate and of polyglycol fatty alcohol ether | 100 g |
| diAndhylformamide | 50 g |
| xylene | 575 g |

The concentrated suspensions, which can also be applied by spraying, are prepared so as to obtain a stable fluid product which does not deposit, and they usually contain from 10 to 75% active material, from 0.5 to 15% surfactants, from 0.1 to 10% thixotropic agents and from 0 to 10 suitable additives, such as anti-foam agents, corrosion inhibitors, stabilizers, penetration agents and adhesives, and, as support, water or an organic liquid in which the active material is only sparingly soluble or is insoluble: certain solid organic materials or inorganic salts can be dissolved in the support in order to help prevent sedimentation, or as antifreezes for the water.

By way of example, here is a concentrated suspension composition:

Example CS 1

| | |
|---|---|
| active material | 500 g |
| polyethoxylated tristyrylphenol phosphate | 50 g |
| polyethoxylated alkylphenol | 50 g |
| polysodium carboxylate | 20 g |
| ethylene glycol | 50 g |
| organopolysiloxane oil (antifoaming agent) | 1 g |
| polysaccharide | 1.5 g |
| water | 316.5 g |

The wettable powders (or powder for spraying) are usually prepared such that they contain 20 to 95% active material, and they usually contain, in addition to the solid support, from 0 to 30% of a wetting agent, from 3 to 20% of a dispersant and, where necessary, from 0.1 to 10% of one or more stabilizers and/or other additives, such as penetration agents, adhesives, anticaking agents, dyes, etc.

In order to obtain the powders for spraying or the wettable powders, the active materials are intimately mixed with the additional substances in suitable mixers and are ground in mills or other suitable grinders. Powders for spraying are thus obtained with advantageous wettability and suspension formation; they can be suspended in water at any desired concentration and these suspensions can be used very advantageously in particular for application to plant leaves.

Pastes can be prepared instead of wettable powders. The conditions and methods for preparing and using these pastes are similar to those for the wettable powders or powders for spraying.

By way of example, here are various compositions of wettable powders (or powders for spraying):

Example WP 1

| | |
|---|---|
| active material | 50% |
| ethoxylated fatty alcohol (wetting agent) | 2.5% |
| ethoxylated phenylethylphenol (dispersant) | 5% |
| chalk (inert support) | 42.5% |

Example WP 2

| | |
|---|---|
| active material | 10% |
| synthetic C13 oxo alcohol of branched type, ethoxylated with 8 to 10 [lacuna] ethylene oxide (wetting agent) | 0.75 |
| neutral calcium lignosulfonate (dispersant) | 12% |
| calcium carbonate (inert filler) | qs 100% |

Example WP 3

This wettable powder contains the same ingredients as in the above example, in the following proportions:

| | |
|---|---|
| active material | 75% |
| wetting agent | 1.50% |
| dispersant | 8% |
| calcium carbonate (inert filler) | qs 100% |

Example WP 4

| | |
|---|---|
| active material | 90% |
| ethoxylated fatty alcohol (wetting agent) | 4% |
| ethoxylated phenylethylphenol (dispersant) | 6% |

Example WP 5

| | |
|---|---|
| active material | 50% |
| mixture of anionic and nonionic surfactants (wetting agent) | 2.5% |
| sodium lignosulfonate (dispersant) | 5% |
| kaolin clay (inert support) | 42.5% |

The aqueous emulsions and dispersions, for example the compositions obtained by diluting a wettable powder or an emulsifiable concentrate according to the invention with water, are included in the general context of the present invention. The emulsions can be of water-in-oil or oil-in-water type and they can have a thick consistency such as that of a "mayonnaise".

The compounds according to the invention can be formulated in the form of water-dispersible granules, which are also included in the context of the invention.

These dispersible granules, with an apparent density generally of between about 0.3 and 0.6, have a particle size generally of between about 150 and 2000 microns and preferably between 300 and 1500 microns.

The active material content of these granules is generally between about 1% and 90% and preferably between 25% and 90%.

The rest of the granule is composed essentially of a solid filler and optionally of surfactant adjuvants which give the granule water-dispersibility properties. These granules can be essentially of two distinct types depending on whether or not the filler selected is water-soluble. When the filler is water-soluble, it can be inorganic or, preferably, organic. Excellent results have been obtained with urea. In the case of an insoluble filler, it is preferably inorganic, such as, for example, kaolin or bentonite. It is then advantageously accompanied by surfactants (in a proportion of from 2 to 20% by weight of the granule), more than half of which consists, for example, of at least one dispersant, which is essentially anionic, such as an alkali metal or alkaline-earth metal polynaphthalene sulfonate or an alkali metal or alkaline-earth metal lignosulfonate, the remainder consisting of nonionic or anionic wetting agents such as an alkali metal or alkaline-earth metal alkyl naphthalene sulfonate.

Moreover, although this is not essential, other adjuvants such as antifoaming agents can be added.

The granule according to the invention can be prepared by mixing together the necessary ingredients, followed by granulation according to several techniques that are known per se (blender, fluid bed, atomizer, extrusion, etc.). The process generally ends by a crushing operation, followed by screening to the particle size chosen within the range mentioned above. Granules obtained as above and then impregnated with a composition containing the active material can also be used.

Preferably, the granule is obtained by extrusion, working as indicated in the examples below.

Example DG1

Dispersible Granules

90% by weight of active material and 10% of urea pellets are mixed together in a mixer. The mixture is then ground in a spindle mill. A powder is obtained which is moistened with about 8% by weight of water. The wet powder is extruded through a perforated-roll extruder. A granulate is obtained, which is dried and then crushed and screened, so as to retain only the granules between 150 and 2000 microns in size, respectively.

Example DG2

Dispersible Granules

The constituents below are mixed together in a mixer:

| | |
|---|---|
| active material | 75% |
| wetting agent (sodium alkyl-naphthalene sulfonate) | 2% |
| dispersant (sodium polynaphthalene sulfonate) | 8% |
| water-insoluble inert filler (kaolin) | 15% |

This mixture is granulated in a fluid bed in the presence of water, then dried, crushed and screened so as to obtain granules between 0.15 and 0.80 mm in size.

These granules can be used alone, or in solution or dispersion in water so as to obtain the desired dose. They can also be used to prepare combinations with other active materials, in particular antibacterial agents, the latter being in the form of wettable powders or aqueous suspensions or granules.

As regards the compositions which are suitable for storage and transportation, they more advantageously contain from 0.5 to 95% (by weight) of active substance.

The invention also relates to a process for the therapeutic antibacterial treatment of man or animals by administration of an effective dose of the peptide according to the invention, in free form or, where appropriate, in the form of addition salts with an acid, Andallic salts or addition salts with a base which are pharmaceutically acceptable, in pure form or in the form of a composition in which it is combined with any other pharmaceutically compatible product, which can be inert or physiologically active. The medicaments according to the invention can be administered orally, parenterally, rectally or topically.

Tablets, pills, powders (in particular in gelatin capsules or cachets) or granules can be used as solid compositions for oral administration. In these compositions, the active product according to the invention is mixed with one or more inert diluents, such as starch, cellulose, sucrose, lactose or silica. These compositions can also comprise other substances, for example one or more lubricants such as magnesium stearate or talc, a dye, a coating (dragees) or a glaze.

Pharmaceutically acceptable solutions, suspensions, emulsions, syrups and elixirs containing inert diluents such as water, ethanol, glycerol, plant oils or liquid paraffin can be used as liquid compositions for oral administration. These compositions can also comprise other substances, for example wetting products, sweeteners, thickeners, flavorings or stabilizers.

The sterile compositions for parenteral administration can preferably be emulsions, suspensions or aqueous or non-aqueous solutions. Water, propylene glycol, a polyethylene glycol, plant oils, in particular olive oil, and suitable organic esters can be used as solvent or vehicle. These compositions can also contain adjuvants, in particular wetting agents, tonicity agents, emulsifiers, dispersants and stabilizers. The sterilization can be carried out in different ways, for example by aseptic filtration, by incorporating sterilizing agents into the composition, by irradiation or by heating. They can also be prepared in the form of sterile solid compositions which can be dissolved in an injectable sterile medium at the time of use.

The compositions for rectal administration are suppositories or rectal capsules which contain, besides the active peptide, excipients such as cocoa butter, semi-synthetic glycerides or polyethylene glycols.

The sterile compositions for topical administration can be, for example, creams, ointments, lotions, eyedrops, mouthwashes, nasal drops or aerosols.

In human therapy, the peptide according to the invention is particularly useful in antibacterial treatments. The doses depend on the desired effect and the duration of the treatment; they are generally between 50 and 1000 mg per day via the oral route for an adult, taken in one or more doses.

In general, the doctor will determine the dosage which he or she considers to be the most appropriate, depending on the age and weight and all the other personal factors of the individual to be treated.

The examples which follow, which are given without any limitation being implied, illustrate the compositions according to the invention.

Example A

Tablets containing a 50 mg dose of active peptide and having the following composition are prepared according to the usual technique:

| | |
|---|---|
| androctonine peptide M1 | 50 mg |
| starch | 60 mg |
| lactose | 50 mg |
| magnesium stearate | 2 mg |

Example B

An injectable solution containing 20 mg of active peptide and having the following composition is prepared:

| | |
|---|---|
| androctonine peptide M 2 | 22.4 mg |
| distilled water | qs 2 cm$^3$ |

What is claimed is:

1. A method for treating a bacterial or fungal infection in an animal comprising administering a peptide of the formula:

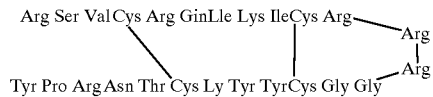

to an animal in need of such treatment.

2. The method of claim 1 wherein said animal is human.

* * * * *

UNITED STATES PATENT AND TRADEMARK OFFICE
CERTIFICATE OF CORRECTION

PATENT NO. : 6,331,522 B1 Page 1 of 1
DATED : December 28, 2001
INVENTOR(S) : Bulet et al.

It is certified that error appears in the above-identified patent and that said Letters Patent is hereby corrected as shown below:

Column 6,
Line 52, "diAnhylformamide" should read -- dimethylformamide --

Column 7,
Line 57, please delete the term "lacuna"

Signed and Sealed this

Eighth Day of October, 2002

Attest:

Attesting Officer

JAMES E. ROGAN
Director of the United States Patent and Trademark Office

SEQUENCE LISTING

<160> NUMBER OF SEQ ID NOS: 2

<210> SEQ ID NO 1
<211> LENGTH: 25
<212> TYPE: PRT
<213> ORGANISM: Androctonus australis

<400> SEQUENCE: 1

Arg Ser Val Cys Arg Gln Ile Lys Ile Cys Arg Arg Arg Gly Gly
 1               5                  10                  15

Cys Tyr Tyr Leu Cys Thr Asn Arg Pro Tyr
                 20                  25

<210> SEQ ID NO 2
<211> LENGTH: 25
<212> TYPE: PRT
<213> ORGANISM: Androctonus australis
<220> FEATURE:
<221> NAME/KEY: UNSURE
<222> LOCATION: (4)...(4)
<221> NAME/KEY: UNSURE
<222> LOCATION: (10)...(10)
<221> NAME/KEY: UNSURE
<222> LOCATION: (16)...(16)
<221> NAME/KEY: UNSURE
<222> LOCATION: (20)...(20)

<400> SEQUENCE: 2

Arg Ser Val Xaa Arg Gln Ile Lys Ile Xaa Arg Arg Arg Gly Gly
 1               5                  10                  15

Xaa Tyr Tyr Lys Xaa Thr Asn Arg Pro Thr
                 20                  25